(12) United States Patent
Himmelsbach et al.

(10) Patent No.: US 6,703,043 B1
(45) Date of Patent: *Mar. 9, 2004

(54) SUBSTANCE RELEASE DEVICE

(75) Inventors: Peter Himmelsbach, Buxtehude (DE); Detlev Radloff, Hamburg (DE)

(73) Assignee: Beiersdorf AG (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/601,631
(22) PCT Filed: Jan. 29, 1999
(86) PCT No.: PCT/EP99/00582
§ 371 (c)(1), (2), (4) Date: Aug. 4, 2000
(87) PCT Pub. No.: WO99/39701
PCT Pub. Date: Aug. 12, 1999

(30) Foreign Application Priority Data

Feb. 6, 1998 (DE) .......................... 198 04 604

(51) Int. Cl.⁷ ............................ A61F 13/00; A61F 13/02
(52) U.S. Cl. ...................... 424/449; 424/443; 424/448; 514/964
(58) Field of Search ................ 424/449, 443, 424/484, 485, 448; 514/964, 945

(56) References Cited

U.S. PATENT DOCUMENTS

| 4,915,950 | A | * | 4/1990 | Miranda et al. | ............ 424/448 |
|---|---|---|---|---|---|
| 5,286,781 | A | | 2/1994 | Gotoh et al. | ................. 524/505 |
| 5,405,622 | A | * | 4/1995 | Vernice et al. | ............... 424/711 |
| 5,418,052 | A | * | 5/1995 | Sugie et al. | ................. 428/261 |
| 5,527,536 | A | | 6/1996 | Merkle et al. | ............... 424/488 |
| 5,618,883 | A | * | 4/1997 | Plamthottam et al. | ......... 525/98 |
| 5,686,099 | A | * | 11/1997 | Sablotsky et al. | ........... 424/499 |
| 5,914,282 | A | * | 6/1999 | Dunshee et al. | ............... 442/76 |

FOREIGN PATENT DOCUMENTS

| DE | 42 24 325 C1 | 2/1994 | ........... A61L/15/58 |
|---|---|---|---|
| EP | 0 914 820 A1 | 5/1999 | ............ A61K/9/70 |

OTHER PUBLICATIONS

Chemical Abstracts, vol. 124, No. 16, dated Apr. 15, 1996, Columbus, Ohio, US; Abstract No. 212122, Seite 709; Spalte 1; XP 002106640 siehe Zusammenfassung & JP 00 803032 A (Bando Chemical Ind.) Jan. 9, 1996.

Derwent Publications Ltd., London, GB; AN 90–372979 XP002106641 & JP 02 270818 A (Sekisui Chem. Ind. Co. Ltd.), Nov. 5, 1990.

* cited by examiner

*Primary Examiner*—Michael G. Hartley
*Assistant Examiner*—Sharmila S Gollamudi
(74) *Attorney, Agent, or Firm*—Norris, McLaughlin & Marcus

(57) ABSTRACT

The invention relates to a device for releasing active agents, characterized in that at a frequency of 0.1 rad/s, it has a glass transition temperature of less than 15° C., contains at least 3% by weight of an SEPS block copolymer and contains at least one substance with a local or systematic effect which does not cause hyperaemia. The device is not foamed.

25 Claims, No Drawings

SUBSTANCE RELEASE DEVICE

CROSS-REFERENCE TO RELATED APPLICATIONS

This application is a national phase filing of and claims the benefit of PCT/EP99/00582 filed Jan. 29, 1999.

The invention relates to a device for releasing at least one substance. One particular embodiment constitutes a backing material and, applied at least partially thereon, a device in the form of an adhesive composition comprising the one or more active substances that are delivered to the skin.

Transdermal therapeutic systems (TTS) are forms of administration of medicaments that deliver one or more medicaments to the skin over a defined period at their location of use. A distinction is made here between systemic and local administration forms.

With systemic administration forms, the active substance passes through the skin into the bloodstream by diffusion and can act within the body as a whole. Local administration forms, on the other hand, act only at the sites of application. The active substance remains in the skin or in the underlying layers.

Strongly adhering plasters are normally coated over their entire area with a rubber adhesive composition. The sticking of such products to the skin gives rise, following their removal, to marked skin irritations and mechanical stressing of the skin. Without auxiliary media it is impossible to break the bond painlessly. In some cases, there are allergic reactions. Furthermore, the adhesive compositions used often lead to a transfer of composition onto the skin.

The use of skin-friendly adhesive compositions, such as acrylate adhesive compositions and hydrogels, is out of the question because of their low shear stability and tack. Improvement through aftertreatment, especially crosslinking, though possible, nevertheless gives a result which is unsatisfactory overall. The proprioreceptive effect is less than that of systems with a rubber adhesive composition.

Other known adhesive systems based on conventional block copolymers are however not skin-friendly, owing to the high level of stabilizer added, or because of the high levels of cohesiveness have been found suitable to date only for industrial applications; alternatively, they cannot be formulated for strong adhesion and sticking to the skin.

The abovementioned adhesive compositions are pressure-sensitive self-adhesive compositions which may be present in a carrier matrix for processing. The term carrier matrix is understood to refer to common organic or inorganic solvents or dispersion media.

Systems without a carrier matrix are referred to as 100% systems and are likewise not unknown. A common mode of processing is that of the melt. Pressure-sensitive hot melt adhesive compositions of this kind have also already been described in the prior art. They are based on natural or synthetic rubbers and/or other synthetic polymers.

An advantage of the 100% systems is that they avoid an operation of removing the carrier matrix, i.e. the auxiliary media, thereby raising the productivity of processing and at the same time reducing the expenditure on machinery and the energy costs. In addition, this reduces the occurrence of residues of the carrier matrix, which, in turn, is beneficial to a reduction in the allergenic potential.

Because of their high level of hardness, sticking to the skin is a problem for such 100% systems.

It is also known to apply such self-adhesive compositions not only over the entire area but also in the form of a pattern of dots, for example by screen printing (DE-C 42 37 252), in which case the dots of adhesive can also differ in their size and/or distribution (EP-B 353 972), or by intaglio printing, in lines which interconnect in the longitudinal and transverse directions (DE-C 43 08 649).

The advantage of the patterned application is that the adhesive materials, given an appropriately porous backing material, are permeable to air and water vapour and, in general, are readily redetachable.

A disadvantage of these products, however, is that if the area covered by the adhesive film, which is impermeable per se, is too large there is a corresponding reduction in the permeability to air and water vapour; the consumption of adhesive composition rises, and, if the area covered by the adhesive film is small, the adhesion properties deteriorate, i.e. the product is detached too readily from the substrate, especially in the case of heavy, textile backing materials.

Numerous embodiments of active substance plasters have already been described in the prior art, some of them operating in accordance with the reservoir principle, where the active substance is delivered, for example, by way of a membrane, in some cases also with a matrix system or with a relatively complex multilayer structure.

It is also known that the adhesive composition of the plaster can be employed as the matrix comprising active substance. In addition to self-adhesive compositions applied from solution, hotmelt self-adhesive compositions have also been proposed for this purpose, as for example in EP-A 663 431, EP-A 452 034, EP-A 305 757, DE-A 43 10 012, DE-A 42 22 334 and DE-C 42 24 325. The active substances listed in these documents, if named at all, have been systemic ones.

Examples of active substance plasters are antimycotic and keratolytic active substance plasters and those which aid the circulation.

However, plasters of this kind, which occasionally have to be applied over a relatively large area, in some cases exhibit distinct mechanical skin irritations after removal in the case of sensitive patients. In some cases there are allergic reactions. After a prolonged period of wear, their removal is to some extent painful.

A further disadvantage of the known thermally active plasters with an adhesive composition based on natural rubber, which is applied in the form of a solution with organic solvents to the plaster backing, is the comparatively low rate of release of the active substance.

The abovementioned disadvantages, and more, also apply to active substance plasters comprising substances other than those mentioned.

For instance, WO 94/02123 describes an active substance plaster based on pressure-sensitive hotmelt adhesive compositions and comprising low-melting and/or readily volatile active substances in a concentration of from 2.5 to 25% by weight. The polymers employed in that document are A-B-A triblock styrene-ethylene-butylene-styrene block copolymers which are notable for low initial tack and low bond strength on skin.

EP 0 663 431 A2, EP 0 443 759 A3, EP 0 452 034 A2 and U.S. Pat. No. 5,371,128 describe uses of pressure-sensitive hotmelt adhesives, based on silicone, with diverse additives and in differentiated forms of construction.

DE 43 10 012 A1 describes the construction of a dermal therapeutic system from meltable poly(meth)acrylate mixtures.

In particular, difficulties are apparent in the release of two or more active substances from polymer systems formed from only one type of polymer. Systems with two or more types of polymer, however, are critical in terms of their compatibility.

DE 43 16 751 C1 describes a multi-chamber system for administering active substances.

EP 0 439 180 describes an active substance plaster for administering tolubuterol.

EP 0 305 757 describes an active substance plaster for administering nicotine.

EP 0 305 758 describes an active substance plaster for administering nitroglycerine.

EP 0 305 756 describes a device for releasing substances, and the preparation and use thereof.

DE 37 43 945 describes a device for delivering substances, and the preparation process. In the case of the pressure-sensitive hotmelt adhesive composition described, which is based on SIS, the device is not self-adhesive. The processing ranges indicated therein lie well below those of hotmelt adhesive compositions and for such systems described would not provide sufficient anchorage of the adhesive composition.

WO 96/22083 indicates a polyisobutylene adhesive for transdermal purposes, having a tackifier with a high glass transition point. The adhesive is not foamed.

JP 07-196505 describes the administration of indomethacin in hotmelt pressure-sensitive adhesives. In this case, a polyethylene foam is used as backing material.

EP 0 428 017 describes an adhesive composition based on SEBS and SEPS block copolymers. There is no description, however, of the release of substances with a local or systemic action.

U.S. Pat. No. 5,085,655 describes the use of SEPS block copolymers as a cohesive sticking system, especially of nappies and panty liners. The possibility of releasing substances is not described.

JP 09 188 865 describes a system based on synthetic block polymers. The release of substances is not described.

JP 08277382 describes a system based on SEPS which is used as a hotmelt adhesive composition for nappies and sanitary towels. The release of substances is not described.

JP 08209094 describes a system based on synthetic block polymers. The release of substances is not described.

JP 03160083 describes a system based on SEPS which is used as a hotmelt adhesive composition for nappies and sanitary towels. The release of substances is not described.

The object of the invention is therefore to provide a device which comprises one or more active substances and which, while avoiding the disadvantages known from the prior art, features a high level of efficacy, i.e. a relatively high rate of release, even in the case of different combinations of active substances, and good skin compatibility coupled with good adhesion. In addition, the device should be able to be prepared in a technically simple and environmentally compatible manner.

This object is achieved by a device for releasing substances as is set out in the main claim. The subclaims relate to advantageous embodiments of the devices of the invention. The invention also embraces processes for producing such devices.

The invention accordingly provides a device for releasing active substances which at a frequency of 0.1 rad/s has a glass transition temperature of less than 15° C. and an SEPS block copolymer content of at least 3% by weight and comprises at least one locally or systemically acting substance, in the preferred embodiment a variety of active substances. The active substance or substances are not hyperaemic; furthermore, the device should not be foamed.

SEPS here stands for styrene-ethylene-propylene-styrene, comprising a block copolymer on the basis of polystyrene blocks (S) and blocks of hydrogenated polyisoprene (EP) or hydrogenated poly(butadiene-co-isoprene) (EEP). Diblocks, triblocks and multiblocks may be used.

In one advantageous embodiment the device has an A/B diblock fraction of more than 30%, preferably greater than 60%.

Preferably, the quantitative concentrations of the active substance or substances in the adhesive composition lie between 0.01 to [sic] about 60% by weight, preferably from 0.1 to 20% by weight.

By active substances in the context of the present invention are meant chemical elements and organic and inorganic compounds which are able to migrate from the constituents of a generic device that comprise them and so bring about a desired effect. Among the fields of use of the device of the invention, human and veterinary medicine are of particular importance, and in this context a configuration of the invention in plaster form is particularly preferred.

Typical active substances—with no claim to completeness—for the production of plaster systems doped with active substance are, in the context of the present invention, as follows:

| Indication: | Active substance |
|---|---|
| Antimycotics | nafitine [sic] |
| | amorrolfine [sic] |
| | tolnaftate |
| | ciclopirox |
| Antiseptics | thymol |
| | eugenol |
| | triclosan |
| | hexachlorophen |
| | benzalkonium chloride |
| | clioquinol |
| | quinolinol |
| | undecenoic acid |
| | ethacridine |
| | chlorohexidine |
| | hexetidine |
| | dodicine |
| | iodine |
| Nonsteroidal antirheumatics | glycol salicylate |
| | flufenamic acid |
| | etofenamate |
| | ketoprofen |
| | piroxicam |
| | indomethacin |
| Antipruritics | polidocanol |
| | isoprenaline |
| | crotamiton |
| Local anaesthetics | benzocaine |
| Antipsoriatics | ammonium bitumasulphonate |
| Keratolytics | urea |

The active substances are dispersed in the device preferably in a thermal homogenizer, such as thermal mixers, thermal kneading apparatus, roll mills or screw systems, for example. The active substance can be added to the ready-produced device. The active substance can also, for example, be incorporated into an intermediate stage or into the initial mixture.

The device is advantageously an adhesive composition which in a particularly preferred embodiment is a hotmelt adhesive composition having an SEPS block copolymer fraction of at least 3% by weight. In one preferred embodiment, triblock copolymers are used. For specific devices, SEP diblock or multiblock polymers are advantageous.

The bonding properties can be adjusted depending on the field of use. In certain cases, strongly self-adhering systems or else systems with pressure-sensitive adhesion are required. To make these adjustments, appropriate additives are added to the polymer system, such as tackifier resins, plasticizers, stabilizers and other auxiliaries.

Their softening point should be higher than 50° C., since the application temperature is generally at least 70° C., preferably between 90 and 150° C. If desired, subsequent crosslinking by irradiation with UV or electron beams may be appropriate. This depends on the specific composition of the main polymer or the additives thereto.

It is particularly advantageous for further polymers to be present in the device, these polymers preferably being based on block copolymers. Blends of block copolymers based on SEPS and SEBS, in particular, are notable for their diverse possibilities for variation, since the targeted reduction in the glass transition temperature of the self-adhesive composition, as a result of the selection of tackifiers, plasticizers, polymer molecule size and molecular distribution of the components employed, ensures the necessary bonding with the skin in a manner appropriate to their function, even at critical sites on the human locomotor system.

The high shear strength of the hotmelt self-adhesive composition is achieved by the cohesive character of the polymer. The good tack results from the range of tackifiers and plasticizers employed.

For systems which adhere particularly strongly the hotmelt self-adhesive composition is based preferably on block copolymers, especially A-B or A-B-A block copolymers or mixtures thereof. The hard phase A is primarily polystyrene or its derivatives and the soft phase B comprises at least one soft phase B based on ethylene, butylene, propylene, isoprene, butadiene or mixtures thereof.

As a further preference, the polymers and the device are constructed on the basis of diblock (A-B) and/or triblock (ABA) copolymers, with a fraction of diblock copolymers of less than 80% by weight.

The chain of phase B may also include sections of other types, such as isoprene, butadiene or similar substances, for example. Polystyrene blocks may also be present in the soft phase B, in an amount of up to 20% by weight. The overall proportion of styrene, however, should always be less than 35% by weight. Preference is given to styrene contents of between 3% by weight and 30% by weight, since a lower styrene content makes the adhesive composition smoother.

The controlled blending of diblock and triblock copolymers is particularly advantageous, preference being given to a proportion of diblock copolymers of less than 80% by weight.

The adhesive composition may also include auxiliaries for particular release, or to assist such release. Examples here are polypropylene glycol and polyethylene glycol.

In one advantageous embodiment, the hotmelt self-adhesive composition having a SEPS block copolymer proportion of at least 3% by weight has the composition indicated below:

from 3 to 90% by weight of block copolymers,
from 5 to 80% by weight of tackifiers, such as aliphatic hydrocarbon resins, hydrogenated terpene resins, hydrogenated hydrocarbon resins, cyclopentadiene resins, styrene-α-methylstyrene resins and low molecular mass polyisobutylenes,
less than 60% by weight of plasticizers, such as paraffin oils, aliphatic hydrocarbon oils, waxes and fatty acetates and alcoholates,
less than 15% by weight of additives,
less than 20% by weight of active substance release auxiliaries, and
less than 5% by weight of stabilizers,
less than 60% by weight of active substance or substances.

The tackifiers and plasticizers serve to establish the bonding properties and the stability. If desired, further stabilizers and other auxiliaries are employed.

The following polymer/tackifier combinations are given by way of example.

|  | Type | E1 | E2 | E3 |
|---|---|---|---|---|
| SEPS (Kuraray Co.) | T1 | 30 | 10 |  |
| Styrene content 13% | T2 |  | 20 | 40 |
| SEBS (Shell) | T3 | 5 |  |  |
| Styrene content 30% | T4 |  | 5 |  |
| Hydrocarbon resin |  | 40 | 49 | 40 |
| Hydrocarbon oil |  | 24 | 15 | 19 |
| Antioxidant |  | 1 | 1 | 1 |

Combinations of other polymer systems are obvious to the person skilled in the art.

It is possible to fill the adhesive composition with mineral fillers, fibres or hollow or solid microbeads.

The hotmelt self-adhesive composition has a softening point of more than 50° C., preferably from 70 to 220° C. and, with very particular preference, from 75 to 140° C.

The dynamic glass transition temperature of the elastomer phase of the adhesive matrix, at a frequency of 0.1 rad/s, is less than 15° C., preferably from −3 to −30° C. and, with particular preference, from −9 to −25° C.

Plasters in particular are subject to stringent requirements in terms of their bonding properties. For ideal application, the hotmelt self-adhesive composition should possess a high tack. There should be functionally appropriately bond strength to the skin and to the reverse of the backing. So that there is no slipping, the hotmelt self-adhesive composition is also required to be of high shear strength.

The targeted reduction in the glass transition temperature of the self-adhesive composition, as a result of the selection of the tackifiers, plasticizers, polymer molecule size and molecular distribution of the components employed, achieves the necessary bonding, appropriate to its function, with the skin and with the reverse of the backing.

The high shear strength of the self-adhesive composition employed here is achieved by the high cohesiveness of the block copolymer. The good tack arises from the range of tackifiers and plasticizers that is employed.

Product properties such as tack, glass transition temperature and shear stability can be quantified readily using a dynamomechanical frequency measurement. In this case, use is made of a rheometer controlled by shearing stress. The results of this measurement method give information on the physical properties of a substance by taking into account the viscoelastic component. In this instance, at a preset temperature, the hotmelt self-adhesive composition is set in oscillation between two plane-parallel plates with variable frequencies and low deformation (linear viscoelastic region). Via a pickup control unit, with computer resistance, the quotient (Q=tan δ) between the loss modulus (G", viscous component) and the storage modulus (G', elastic component) is measured.

$$Q = \tan \delta = G''/G'$$

A high frequency is chosen for the subjective sensing of the tack and a low frequency for the shear strength.

A high numerical value denotes better tack and poorer shear stability.

The complex-dynamic glass transition point is the point of transition from the amorphous to the viscoelastic region. It corresponds to the maximum of the temperature function at a predetermined frequency.

| Designation | $T_g$ low frequency | Conformity low frequency/RT | Tack high frequency/RT |
|---|---|---|---|
| Self-adhesive composition A | 4 ± 2° C. | tan δ = 0.08 ± 0.03 | tan δ = 0.84 ± 0.03 |
| Self-adhesive composition B | −9 ± 2° C. | tan δ = 0.32 ± 0.03 | tan δ = 1.70 ± 0.03 |

In accordance with the invention, preference is given to hotmelt self-adhesive compositions for which the ratio of the viscous component to the elastic component at a frequency of 100 rad/s at 25° C. is greater than 0.7, or to hotmelt self-adhesive compositions for which the ratio of the viscous component to the elastic component at a frequency of 0.1 rad/s at 25° C. is less than 0.6, preferably between 0.35 and 0.02 and, with very particular preference, between 0.3 and 0.1.

In exceptional cases, a modified use of the device can be achieved by it being foamed.

In this case, the devices with the active substances added to them are preferably foamed using inert gases such as nitrogen, carbon dioxide, noble gases, hydrocarbons or air, or mixtures of these. In some cases, foaming additionally by thermal decomposition of gas-evolving substances, such as azo, carbonate and hydrazide compounds, has been found suitable.

The degree of foaming, i.e. the gas content, should be at least about 5% by volume and can range up to about 85% by volume. In practice, levels of from 10 to 75% by volume, preferably 50% by volume, have been found appropriate. Operating at a relatively high temperature of approximately 100° C. and with a comparatively high internal pressure produces very open-pored adhesive foam layers which are particularly permeable to air and water vapour.

The advantageous properties of the device include its good conformity even on uneven surfaces, owing to the elasticity and plasticity of the foamed device.

At the same time, the vacuoles in the foam bring about a more than proportional increase in the transportation of the active substances, as a result of which very good release rates are achieved.

A particularly suitable process for producing the device foamed in accordance with the invention operates by the foam mixing system. In this system, the thermoplastic adhesive composition is reacted with the intended gases, such as nitrogen, air or carbon dioxide, for example, in various volume proportions (from about 10 to 80% by volume) in a stator/rotor system under high pressure and at a temperature above the softening point (approximately 120° C.).

Whereas the gas entry pressure is greater than 100 bar, the mixing pressures between gas and thermoplastic in the system are from 40 to 100 bar, preferably from 40 to 70 bar. The pressure-sensitive adhesive foam produced in this way can subsequently pass through a line into the applicator unit. In the applicator unit, commercially customary nozzles, extruder systems or chamber systems are used.

The interaction of the active substances with the skin is, as is known, modulated by enhancers that are mixed into the adhesive composition or intensified by the occlusive effect of adhesive composition and covering. In contrast to this it is possible, with the use of breathable doped coatings in conjunction with elastic and likewise breathable backing materials, in particular for example during sporting activities, to achieve a) a level of wear comfort which is perceived subjectively as more pleasant by the user and b) as a result of an interaction of the skin with the environment (for example suppression of perspiration) that is less disturbed by the release behaviour, a more defined penetration of active substances into the skin.

In contrast, it is also possible by virtue of the processes mentioned here to achieve permeability of the doped plaster system from the outside. By virtue of this property of the product, therefore, it is possible following actual application for substances to be brought to the contact point between doped adhesive/skin, through the backing, even at a later time (sprinkling on of liquid, wiping, etc.). These substances might, for example, comprise an additional enhancer effect or might initiate or attenuate the pharmaceutical action or modulate it appropriately for a favourable consumer response.

By virtue of the foaming of the device and the open pores in the composition which form as a result, and given the use of an inherently porous backing, the products coated with the device are of good permeability to water vapour and air. The amount of device required is considerably reduced without adverse effect and mode of action of the device properties [sic].

Foaming also generally reduces the viscosity of the device. This lowers the melt energy, and even thermally unstable backing materials can be coated directly.

It is also advantageous, especially for use with medical products, if the doped composition is applied partially to the backing material, for example by halftone printing, thermal screen printing, thermal flexographic printing or intaglio printing, because backing materials which have been self-adhesively treated in a continuous applied line may in adverse circumstances induce mechanical skin irritations when applied.

It is also possible, furthermore, to apply the adhesive composition, for example, by spraying, which produces a more or less irregular pattern of application.

Partial application makes it possible, through controlled channels, to dissipate the transepidermal water loss, and improves the removal of sweat from the skin in vapour form, especially when the backing materials used are permeable to air and water vapour. By this means the skins irritations induced by an accumulation of body fluids are avoided. The dissipation channels that have been set up enable fluids to be conducted away.

Preference is given to application in the form of polygeometric domes, especially those where the ratio of diameter to height is less than 5:1. Printed application of other forms and patterns on the backing material is also possible—for example, a printed image in the form of alphanumeric character combinations or patterns such as matrices, stripes and zigzag lines.

The doped composition can be distributed uniformly over the backing material; alternatively, it can be applied with a thickness or density which varies over the area, as appropriate to the function of the product.

The principle of thermal screen printing consists in the use of a rotating, heated, seamless, drum-shaped, perforated, cylindrical screen which is fed via a nozzle with the preferred composition. A specially shaped nozzle lip (circular- or square-section coating bar) presses the composition, which is fed in via a channel, through the perforation of the screen wall and onto the backing web that is conveyed past it. This backing web is guided by means of a counterpressure roller against the external jacket of the heated screen drum at a rate which corresponds to the peripheral speed of the rotating screen drum.

In this process, the formation of the small doped domes takes place by the following mechanism:

The pressure of the nozzle coating bar conveys the doped composition through the screen perforation onto the backing material. The size of the domes formed is determined in advance by the diameter of the screen perforation. The screen is lifted from the backing in accordance with the rate of transportation of the backing web (rotary speed of the screen drum). As a consequence of the high adhesion of the self-adhesive composition and of the internal cohesion of the hotmelt, the limited supply of hotmelt self-adhesive composition in the perforations is drawn in sharp definition from the base of the domes, that is already adhering to the backing, and is conveyed onto the backing by the pressure of the coating bar.

Following the end of this transportation, the more or less highly curved surface of the dome forms over the predefined base area depending on the rheology of the hotmelt self-adhesive composition. The height-to-base ratio of the dome depends on the ratio of the perforation diameter to the wall thickness of the screen drum and on the physical properties (flow behaviour, surface tension and contact angle on the backing material) of the self-adhesive composition.

For the screen in thermal screen printing, the web-to-hole ratio can be less than 3:1, preferably less than or equal to 1:1 and, in particular, equal to 1:3.

The above-described mechanism of formation of the domes requires, preferentially, backing materials that are absorbent or at least wettable by the doped composition. Non-wetting backing surfaces must be pretreated by chemical or physical methods. This can be done by means of additional measures such as corona discharge, for example, or by coating with wetting agents.

Using the printing technique indicated it is possible to lay down the size and shape of the domes in a defined manner. The bond strength values which are relevant for use, which determine the quality of the products formed, are within very narrow tolerances provided that coating is carried out correctly. The base diameter of the domes can be chosen to be from 10 to 5000 μm, the height of the domes is from 20 to 2000 μm, preferably from 50 to 1000 μm, the low-diameter range being intended for smooth backings and the range of greater diameter and greater dome height being intended for rough or highly porous backing materials.

The positioning of the domes on the backing is laid down in a defined manner by the geometry of the applicator unit, for example the gravure or screen geometry, which can be varied within wide limits. With the aid of the parameters indicated it is possible, by way of adjustable variables, to establish with very great precision the desired profile of properties of the coating, harmonized with the various backing materials and applications.

The backing material is preferably coated at a rate of more than 2 m/min, preferably from 20 to 220 m/min, the chosen coating temperature being greater than the softening point.

The doped device can be applied to the backing material with a weight per unit area of greater than 15 $g/m^2$, preferably between 90 and 400 $g/m^2$ and, with very particular preference, between 130 and 300 $g/m^2$.

The percentage area that is coated with the doped device should be at least 20% and can range up to approximately 95%, for specific products preferably from 40 to 60% and from 70 to 95%. This can be achieved, if desired, by means of multiple application, with the possible use if desired of devices having different properties and dopes.

The combination of the doped devices and of the partial coating firstly ensures secure bonding of the medical product to the skin and secondly prevents at least visually discernible allergic or mechanical skin irritations, even in the case of an application which extends over several days.

The epilation of corresponding body regions and the transfer of composition to the skin are negligible owing to the high cohesiveness of the device, since the device is not anchored to skin and hair—rather, the anchorage of the device to the backing material, at up to 12 N/cm (sample width), is good for medical applications.

Because of the intended breakage points that have been formed in the coating, layers of skin are no longer displaced with one another or against one another in the course of detachment. The non-displacement of the layers of skin and the relatively low level of epilation lead to an unprecedented degree of painlessness in such strongly adhering systems. In addition, the individual biomechanical control, which results in a demonstrable reduction in the bond strength of this device, assists detachability.

Depending on the backing material and its temperature sensitivity, composition can be applied directly or can be applied first to an auxiliary support and then transferred to the ultimate backing.

Subsequent calendering of the coated product and/or pretreatment of the backing, such as corona irradiation, for better anchorage of the adhesive layer, may also be advantageous.

In addition, treating the composition by electron beam post-crosslinking or by UV irradiation can lead to an improvement in the desired properties.

Suitable backing materials are all rigid and elastic sheetlike structures of synthetic and natural raw materials. Preference is given to backing materials which, following the application of the adhesive composition, can be employed in such a way that they fulfil the characteristics of a functional dressing.

Examples are textiles such as wovens, knits, lays, nonwovens, laminates, nets, films, foams and papers. In addition, these materials can be pretreated or aftertreated. Common pretreatments are corona and hydrophobicization; customary aftertreatments are calendering, thermal conditioning, laminating, punching and covering.

The backing material coated with the composition can have an air permeability of greater than 1 $cm^3/(cm^{2*}s)$, preferably greater than 15 $cm^3/(cm^{2*}s)$ and, with very particular preference, greater than 70 $cm^3/(cm^{2*}s)$, and a water vapour permeability of greater than 500 $g/(m^{2*}24\ h)$, preferably greater than 1000 $g/(m^{2*}24\ h)$ and, with very particular preference, greater than 2000 $g/(m^{2*}24\ h)$.

Finally, following the coating operation, the device can be covered with an anti-adhesive backing material, such as siliconized paper, or provided with a wound pad or with padding.

Subsequently, the device is punched out in the desired size.

It is particularly advantageous if the device is sterilized, preferably by means of γ (gamma) radiation. This is particularly suitable for subsequent sterilization of a block copolymer-based polymer system containing no double bonds. This applies in particular to the styrene-propylene-ethylene-styrene block copolymer of the invention. In this case the properties are not subject to any changes that are significant for the application.

The device of the invention can have a bond strength of at least 1.5 N/cm, in particular a bond strength of between 2.5 and 5 N/cm. Higher bond strengths may be achieved on other substrates.

The intention in the text below is to describe particularly advantageous embodiments of the invention, without wishing thereby unnecessarily to restrict the invention.

In accordance with the invention, example formulations for releasing various active substances were prepared. All formulations were prepared without solvent in a laboratory kneading apparatus at a temperature of between 90° C. and 180° C. The pharmaceutical active substance was added during the cooling phase at a temperature which in the case of solid pharmaceuticals was approximately 10° C. above the respective melting point. The production of laboratory samples for testing the formulations was carried out with the aid of a hot press.

EXAMPLE 1

5% by Weight Active Substance Preparation 39.0 g of Septon 4033 (Kuraray), 57.0 g of Regalite 91 (Hercules), 46.5 g of Hercules MBG 274 (Hercules) and 1.4 g of Irganox 1010 (Ciba) were melted in a laboratory kneading apparatus at 150° C. and homogenized over a period of approximately 90 minutes. Subsequently, at 100° C., 7.5 g of ibuprofen were added and the mixture was homogenized for a further 60 minutes. The hot mass was subsequently poured into a siliconized pan.

To produce laboratory samples, 10.0 g of the cooled mass were pressed in a melt press at 100° C. between two siliconized release paper sheets to a layer thickness of 400 μm. Subsequently, following removal of the release paper, one side of the adhesive layer was laminated with siliconized polyester film. On the opposite side, an adhesive polyester film was laminated. The specimens for determining the bond strength and the release of active substance were prepared from this sample.

The result was a colourless, transparent sample having excellent bond strength and very good cohesion. The bond strength, measured on PMMA (polymethyl methacrylate) in the 90° peel test, was 18.7 N/cm at a peel rate of 300 mm/min.

The release of active substance was determined by means of a Keshary-Chien cell using a silicone membrane and an aqueous phosphate buffer as receptor phase. Over a period of 24 h, 281 $\mu$g/cm$^2$ of the incorporated active substance were released.

EXAMPLES 2 to 6

5% by Weight Active Substance Preparation

The following example formulations were prepared following the procedure of Example 1.

| Example | Active substance | Added at |
|---|---|---|
| 2 | salicylic acid | 160° C. |
| 3 | diclofenac | 160° C. |
| 4 | benzocaine | 100° C. |
| 5 | licocaine *HCl | 130° C. |
| 6 | bufexamac | 160° C. |

EXAMPLES 7 to 9

1% by Weight Active Substance Preparation 40.7 g of Septon 4033 (Kuraray), 59.4 g of Regalite 91 (Hercules), 48.4 g of Hercules MBG 274 (Hercules) and 1.4 g of Irganox 1010 (Ciba) were melted in a laboratory kneading apparatus at 150° C. and homogenized over a period of approximately 90 minutes. Subsequently, at the temperature indicated in the table, 1.5 g of the respective active substance were added and the mixture wasp homogenized for a further 60 minutes. Subsequent processing followed the procedure described under Example 1.

| Example | Active substance | Added at |
|---|---|---|
| 7 | clotrimazole | 150° C. |
| 8 | econazole | 100° C. |
| 9 | diphenhydramine *HCl | 170° C. |

EXAMPLES 10

1% By Weight Active Substance Preparation

In accordance with the invention, an unfoamed substance release device was produced which contained a non-hyperaemic active substance. The active substance used was ibuprofen.

The backing material consisted of a nonelastic cotton fabric having a maximum tensile strength of more than 80 N/cm and an extension at maximum tensile strength of less than 20%.

The composition of this hotmelt pressure-sensitive adhesive composition was as follows:
  an SEPS block copolymer consisting of hard and soft segments, with a styrene content in the polymer of 13 mol %; its proportion in the adhesive composition is 35% by weight (Kuraray Co.)
  a paraffinic hydrocarbon resin whose proportion in the adhesive composition is 63% by weight
  an anti-ageing agent with a proportion of less than 1.0% by weight (Irganox 1010 Ciba)
  ibuprofen with a proportion of 1%.

The components of the adhesive that were employed were homogenized in a thermal mixer at 165° C. for 1.5 hours. The active substance was added in the cooling phase, at 100° C., and homogenization was continued in the mixer for 75 minutes.

The self-adhesive composition was applied with a nozzle over the whole area of the backing. The direct coating operation took place at 50 m/min and at a temperature of 120° C. The backing material was coated with 170 g/m$^2$.

The plaster material produced in this way shows a comparably good release of the active substance (liberation study).

Following application, no skin irritations were found.

What is claimed is:

1. A substance release device comprising at least 3% by weight of a styrene-ethylene-propylene-styrene ("SEPS") block copolymer, additional polymers based on block copolymers having at least one hard phase (A) based on styrene or derivatives thereof and at least one soft phase (B) selected from the group consisting of ethylene, butylenes, propylene, isoprene, butadiene and mixtures thereof constructed on the basis of diblock (A-B) and/or triblock (ABA) having less than 80% by weight diblock copolymers and at least one locally or systemically active substance which does not have a hyperaemic action and is selected from the group consisting of antimycotics, antiseptics, nonsteroidal antiheumatics, antipuritics, local anaesthetics, antipsonatics and keratolytics wherein the copolymer is foamed and has a glass transition temperature of less than 15° C. at a frequency of 0.1 rad/s and is in the form of an adhesive composition and the active is dispersed in the device.

2. Substance release device according to claim 1 wherein the device comprises different active substances.

3. Substance release device according to claim 1 wherein the device comprises from 0.01 to 60% by weight active substance or substances.

4. Substance release device according to claim 1 wherein the overall styrene content in the polymer system is less than 35% by weight.

5. Substance release device according to claim 1 wherein the device is a hotmelt adhesive composition having an SEPS block copolymer proportion of at least 3% by weight and consisting of
   a) from 3 to 90% by weight of block copolymers,
   b) from 5 to 80% by weight of tackifiers,
   c) less than 60% by weight of plasticizers,
   d) less than 15% by weight of additives,
   e) less than 5% by weight of stabilizers,
   f) less than 20% by weight of active substance release auxiliaries, and
   g) less than 20% by weight of active substance or substances.

6. Substance release device according to claim 1 wherein the device is applied partially to a backing material by means selected from the group consisting of halftone printing, thermal screen printing, thermal flexographic printing and intaglio printing.

7. Substance release device according to claim 1 wherein the device is applied to a backing material by spraying.

8. Substance release device according to claim 1 wherein the device is applied in the form of polygeometric domes to the backing material.

9. Substance release device according to claim 1 wherein the device is applied to a backing material with a weight per unit area of greater than 15 g/m$^2$.

10. Substance release device according to claim 1 wherein the percentage area on a backing material that is coated with the device is at least 20%.

11. Substance release device according to claim 1 wherein a backing material coated with the device has an air permeability of greater than 1 cm$^3$/(cm$^2$*s).

12. Substance release device according to claim 1 wherein the device is sterilized by means of γ (gamma) radiation.

13. Substance release device according to claim 1 wherein the device has a bond strength of at least 1.5 N/cm.

14. Substance release device of claim 1 wherein the SEPS block copolymer comprises polystyrene blocks ("S") and blocks of hydrogenated polyisoprene ("EP") or hydrogenated poly(butadiene-co-isoprene) ("EEPP") and has an S/EP or S/EEP diblock fraction of more than 30%.

15. Substance release device according to claim 1 comprising 0.1% to 20% by weight active substance or substances.

16. Substance release device according to claim 4 wherein the overall styrene content is between 5% and 30% by weight.

17. Substance release device according to claim 5 wherein the tackifiers are selected from the group consisting of aliphatic hydrocarbon resins, hydrogenated terpene resins, hydrogenated hydrocarbon resins, cyclopentadiend resins and low molecular mass polyisobutylenes.

18. Substance release device according to claim 5 wherein the plasticizers are selected from the group consisting of paraffin oils, aliphatic hydrocarbon oils, waxes and fatty acetates and alcoholates.

19. Substance release device according to claim 1 wherein the dynamic glass transition temperature of the elastomer phase is between −3° C. and −30° C.

20. Substance release device according to claim 1 wherein the dynamic glass transition temperature of the elastomer phase is between −9° C. and −25° C.

21. Substance release device according to claim 9 wherein the backing material has a weight per unit area between 90 g/m$^2$ and 400 g/m$^2$.

22. Substance release device according to claim 9 wherein the backing material has a weight per unit area between 130 g/m$^2$ and 300 g/m$^2$.

23. Substance release device according to claim 10 wherein the percentage area of the backing material coated with the device is between 40% and 60%.

24. Substance release device according to claim 10 wherein the percentage area of the backing material coated with the device is between 70% and 95%.

25. Substance release device according to claim 13 wherein the bond strength is between 2.5 N/cm and 5 N/cm.

* * * * *